United States Patent [19]

Lee

[11] Patent Number: 4,526,608

[45] Date of Patent: Jul. 2, 1985

[54] CERTAIN 2-PYRIDYLOXYPHENYL-OXIMINO-ETHER-CARBOXYLATES, HERBICIDAL COMPOSITIONS CONTAINING SAME AND THEIR HERBICIDAL METHOD OF USE

[75] Inventor: Shy-Fuh Lee, Sunnyvale, Calif.

[73] Assignee: Zoecon Corporation, Palo Alto, Calif.

[21] Appl. No.: 481,044

[22] Filed: Mar. 31, 1983

Related U.S. Application Data

[63] Continuation-in-part of Ser. No. 398,046, Jul. 14, 1982, abandoned, which is a continuation-in-part of Ser. No. 344,168, Jan. 29, 1982, abandoned.

[51] Int. Cl.³ .................. C07D 213/64; A01N 43/40
[52] U.S. Cl. ........................................ 71/94; 546/288; 546/296; 546/297; 546/300; 560/9; 560/21; 562/426; 562/435; 564/166; 564/310; 564/399; 564/430; 260/465 E

[58] Field of Search ............. 546/288, 296, 297, 300; 71/94

[56] References Cited

U.S. PATENT DOCUMENTS 4,364,875 12/1982 Sehring et al. ............... 260/465 E
4,419,124 12/1983 Swithenbank ................... 71/98

FOREIGN PATENT DOCUMENTS 0080746 6/1983 European Pat. Off. ........... 71/94

*Primary Examiner*—Alan L. Rotman
*Attorney, Agent, or Firm*—Hana Dolezalova; Jacqueline S. Larson

[57] ABSTRACT

Substituted phenoxyphenylhydroxyamines and pyridyloxyphenylhydroxyamines, and the use thereof for the control of weeds.

8 Claims, No Drawings

CERTAIN 2-PYRIDYLOXYPHENYL-OXIMINO-ETHER-CARBOXYLATES, HERBICIDAL COMPOSITIONS CONTAINING SAME AND THEIR HERBICIDAL METHOD OF USE

This is a continuation-in-part of Ser. No. 398,046, filed July 14, 1982, abandoned which is a continuation-in-part of Ser. No. 344,168, filed Jan. 29, 1982, abandoned.

This invention relates to substituted phenoxyphenylhydroxyamines and pyridyloxyphenylhydroxyamines, intermediates therefor, and the use of said compounds for the control of weeds.

The novel compounds of the present invention are represented by the following formula (A):

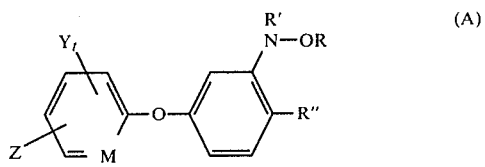

wherein,

M is CH or N;

t is zero, one or two;

each of Y and Z is independently selected from hydrogen, lower alkyl, lower alkoxy, lower haloalkyl, lower haloalkoxy, halogen, cyano and nitro;

R' is independently selected from the values of R; heterocycloalkyl; arylalkyl; or the group

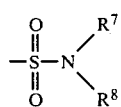

wherein $R^7$ is hydrogen or lower alkyl and $R^8$ is lower alkyl.

R" is nitro, amino, cyano or chloro.

R is hydrogen, lower alkyl, lower alkenyl, lower alkynyl, cycloalkyl, cycloalkalkyl, lower haloalkyl, lower haloalkenyl, lower haloalkynyl, substituted or unsubstituted phenyl, substituted or unsubstituted phenylalkyl, or one of the groups

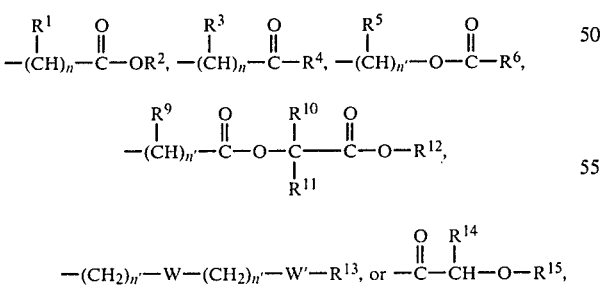

wherein, each of W and W' is independently oxygen or sulfur;

n is zero, one or two; n' is one or two;

$R^1$ is hydrogen, methyl, methoxy or methylthio;

each of $R^2$ and $R^{12}$ is hydrogen, metal cation, lower alkyl, lower alkenyl, lower alkynyl, lower alkylthioalkyl, lower alkoxyalkyl, lower alkylsulfinylalkyl, lower alkylsulfonylalkyl, substituted or unsubstituted phenyl, cycloalkyl, lower haloalkyl, lower alkoxyalkoxyalkyl, lower alkylamino, lower dialkylamino, or $N=C(R^8)_2$;

each of $R^3$ and $R^{14}$ is hydrogen or methyl;

$R^4$ is lower alkyl, lower alkenyl, lower alkylthio, lower alkylamino, cycloalkyl, lower haloalkyl, substituted or unsubstituted phenyl, substituted or unsubstituted benzyl, or substituted or unsubstituted anilino, or the group

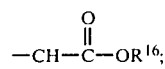

each of $R^5$ and $R^{16}$ is hydrogen or lower alkyl;

$R^6$ is lower alkyl, lower alkoxyalkyl, cycloalkyl, lower haloalkyl, or substituted or unsubstituted phenyl; or together with $R^5$ forms a lower alkylene or a lower alkenylene ring;

$R^{13}$ is lower alkyl;

each of $R^9$, $R^{10}$ and $R^{11}$ is independently selected from hydrogen, lower alkyl, lower alkoxy, or lower alkylthio; and $R^{15}$ is substituted or unsubstituted phenyl, or substituted or unsubstituted phenoxyphenyl.

In the description and claims hereinafter, each of $R-R^{16}$, M, n, n', t, W, W', X, Y and Z is as defined above, unless otherwise specified.

The compounds of formula (A) where R" is nitro may be synthesized as outlined below. (XX=Br or Cl):

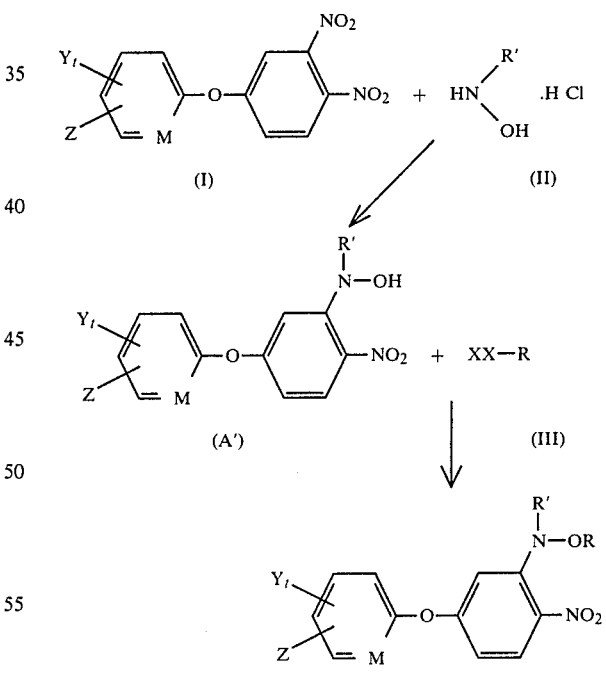

In the above synthesis, a dinitrobenzene (I) is reacted with a hydroxyamine hydrochloride (II), most usually at room temperature, in an organic solvent such as methylene chloride or tetrahydrofuran and a base such as potassium carbonate to give a phenylhydroxyamine (A') (formula A where R is hydrogen). The hydroxyamine (A') is reacted for a halide (III) at room temperature or above in a solvent such as acetone, 2-butanone, methylene chloride or benzene and with or without a base such as triethylamine, potassium carbonate or pyridine to give a compound of formula (A) (where R is other than hydrogen). In the same manner and conditions, the compounds of the present invention may be prepared as follows (XX=Br or Cl):

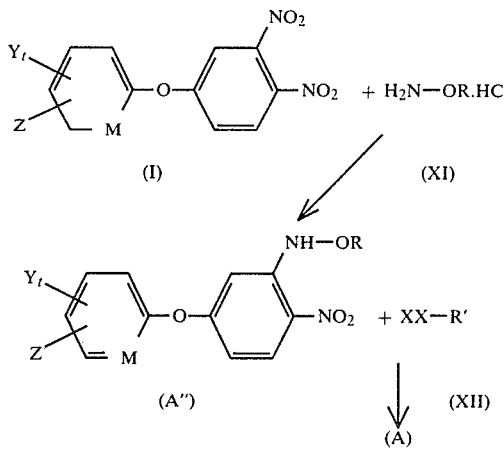

Compounds where R is

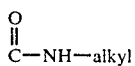

are prepared by reacting a hydroxyamine (A') with an alkylisocyanate at room temperature and in a solvent such as tetrahydrofuran. In the same way, compounds were R' is

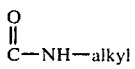

are prepared from a substituted hydroxyamine and an alkylisocyanate.

The compounds of the present invention where R''=cyano or chloro can be produced by the hydrogenation of a compound of formula (A) where R''=nitro to an amino compound (A where R''=amino), which is diazotized following the procedure described in *Org. Synth. Coll.* Vol. 1:514 (1932). The diazo salt is then reacted with cuprous cyanide or cuprous chloride.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The term "lower alkylthio" refers to an alkylthio group, straight or branched, having a chain length of one to eight carbon atoms.

The term "lower alkenyl" refers to an ethylenically unsaturated hydrocarbon group, straight or branched, having a chain length of two to eight carbon atoms and one or two ethylenic bonds.

The term "lower alkylamino" refers to an alkylamino group, straight or branched, having a chain length of one to eight carbon atoms. The term "lower dialkylamino" refers to a dialkylamino group wherein each of the alkyls has a chain length of one to eight carbon atoms.

The term "lower alkynyl" refers to an alkynyl group, straight or branched, having a chain length of two to eight carbon atoms and one or two acetylenic bonds.

The term "cycloalkyl" refers to a cycloalkyl group of three to eight cyclic carbon atoms. The term "cycloalkalkyl" refers to lower alkyl group substituted at one of the carbon atoms by a cycloalkyl group.

The term "heterocycloalkyl" refers to a cycloalkyl group wherein one or two of the carbon atoms is replaced by an atom selected from oxygen or nitrogen.

The term "arylalkyl" refers to a furylalkyl group, a pyranylalkyl group or a pyrrolylalkyl group wherein the alkyl has a chain length of one to three carbon atoms.

The terms "substituted phenyl," "substituted benzyl" or "substituted anilino" refer respectively to a phenyl group, a benzyl group or an anilino group substituted at one, two or three of the ring carbon atoms with a group selected from lower alkyl, lower haloalkyl, lower alkoxy, lower alkenyl, lower haloalkenyl, lower alkenyloxy, halogen, nitro, cyano or lower alkylthio.

The term "substituted phenoxyphenyl" refers to a phenoxyphenyl group substituted at one, two or three of the phenoxy ring carbon atoms with a group selected from lower alkyl, lower haloalkyl, lower alkoxy, lower alkenyl, lower haloalkenyl, lower alkenyloxy, halogen, nitro, cyano or lower alkylthio.

The term "lower alkoxyalkyl" refers to an alkyl group substituted at one of the carbon atoms by an alkoxy group, the total number of carbon atoms being not greater than ten.

The term "lower alkylthioalkyl" refers to an alkyl group substituted at one of the carbon atoms by an alkylthio group, the total number of carbon atoms being not greater than ten.

The term "lower alkylsulfinylalkyl" refers to an alkyl group substituted at one of the carbon atoms by an alkylsulfinyl group, straight or branched, the total number of carbon atoms being not greater than ten. The term "lower alkylsulfonylalkyl" refers to an alkyl group substituted at one of the carbon atoms by an alkylsulfonyl group, straight or branched, the total number of carbon atoms being not greater than ten.

The term "lower alkoxyalkoxyalkyl" refers to an alkyl group substituted at one of the carbon atoms with an alkoxy group which, in turn, is substituted at one of its carbon atoms with an alkoxy group, the total number of carbon atoms being not greater than ten.

The novel compounds of formula (A) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The compounds of the present invention have herbicidal activity on both broad leaf plants and the grassy weeds or graminaceous weeds. The optimum usage of a compound of the present invention is readily determinable by one of ordinary skill in the art using routine testing such as greenhouse testing and small plot testing.

The term "herbicide," as used herein, refers to an active ingredient which modifies the growth of plants because of phytotoxic or plant growth regulating properties so as to retard the growth of the plant or damage the plant sufficiently to kill it.

The following examples are provided to illustrate the practice of the present invention. Temperature is given in degrees Centigrade. "RT" means room temperature.

EXAMPLE 1

A mixture of 4-(2-chloro-4-trifluoromethylphenoxy)-1,2-dinitrobenzene (500 mg, 1.38 mmol), N-methylhydroxyamine hydrochloride (230 mg, 2.76 mmol), potassium carbonate (228 mg, 1.65 mmol) and tetrahydrofuran (THF) (5 ml) is stirred at RT for 72 hours. The reaction mixture is then filtered, and the filtrate is concentrated to dryness. The oily residue is taken up in ether, washed, dried and evaporated to dryness to give, after purification by preparative thin layer chromatography (prep. TLC), N-methyl-N-[2-nitro-5-(2-chloro-4-trifluoromethylphenoxy)phenyl]-hydroxyamine.

nmr(CDCl$_3$) τ6.87 (S,3H,NHC$_3$), 3.60–2.07(m,6H aromatic H).

EXAMPLE 2

Following the procedure of Example 1, each of 4-(4-trifluoromethylphenoxy)-1,2-dinitrobenzene, 4-(2-fluoro-4-trifluoromethylphenoxy)-1,2-dinitrobenzene, 4-(4-chloro-2-nitrophenoxy)-1,2-dinitrobenzene and 4-(2,6-dichloro-4-trifluoromethylphenoxy)-1,2-dinitrobenzene is reacted with N-methylhydroxyamine hydrochloride to yield, respectively,
N-methyl-N-[2-nitro-5-(4-trifluoromethylphenoxy)-phenyl]hydroxyamine,
N-methyl-N-[2-nitro-5-(2-fluoro-4-trifluoromethylphenoxy)phenyl]hydroxyamine,
N-methyl-N-[2-nitro-5-(4-chloro-2-nitrophenoxy)-phenyl]hydroxyamine, and
N-methyl-N-[2-nitro-5-(2,6-dichloro-4-trifluoromethylphenoxy)phenyl]hydroxyamine.

EXAMPLE 3

A mixture of N-methyl-N-[2-nitro-5-(2-chloro-4-trifluoromethylphenoxy)phenyl]hydroxyamine (500 mg, 1.38 mmol), potassium carbonate (228 mg, 1.65 mmol) and methyl bromoacetate (316 mg, 2.07 mmol) in anhydrous acetone (10 ml) is heated under reflux overnight. The reaction is filtered and concentrated, and the oily residue is purified by prep. TLC to give N-methyl-N-[2-nitro-5-(2-chloro-4-trifluoromethylphenoxy)phenyl]-methoxycarbonylmethoxyamine.

nmr(CDCl$_3$) τ6.87(S,3H,NCH$_3$), 6.30(S,3H,OCH$_3$), 5.74(S,2H,OCH$_2$—).

In like manner, a mixture of N-methyl-N-[2-nitro-5-(2-chloro-4-trifluoromethylphenoxy)phenyl]hydroxyamine (700 mg, 1.93 mmol), potassium carbonate (346 mg, 2.50 mmol) and methyl 2-bromopropionate (581 mg, 3.48 mmol) in 2-butanone (15 ml) is heated under reflux for 20 hours. The reaction mixture is filtered, concentrated and purified to give N-methyl-N-[2-nitro-5-(2-chloro-4-trifluoromethylphenoxy)phenyl]methoxycarbonyl-α-ethoxyamine.

nmr(CDCl$_3$) τ8.72(d,3H,

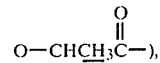

6.94(S,3H,NCH$_3$), 6.37 (S,3H,OCH$_3$), 5.76 (q,1H,

EXAMPLE 4

To a solution of N-methyl-N-[2-nitro-5-(2-chloro-4-trifluoromethylphenoxy)phenyl]hydroxyamine (500 mg, 1.38 mmol) in methylene chloride (2 ml) is added pyridine (0.16 ml, 2.00 mmol) and benzene (3 ml), followed by α,α-dichloropropionyl chloride (328 mg, 1.5 eq.). The mixture is stirred at RT for 2 hours. The resulting reaction mixture is then taken up in methylene chloride, washed, dried and evaporated to dryness. The crude product is purified by prep. TLC to yield N-methyl-N-[2-nitro-5-(2-chloro-4-trifluoromethylphenoxy)phenyl]-α,α-dichloropropionyloxyamine. nmr (CDCl$_3$) τ7.77(S,3H,COC Cl$_2$ CH$_3$), 6.67(S, 3H, NCH$_3$).

EXAMPLE 5

To a solution of N-methyl-N-[2-nitro-5-(2-chloro-4-trifluoromethylphenoxy)phenyl]hydroxyamine (500 mg, 1.38 mmol) in methylene chloride (10 ml) containing triethylamine (0.23 ml, 1.65 mmol) is added, at 0°, ethyl chloroformate (224 mg, 2.07 mmol) in methylene chloride (2 ml). The mixture is stirred at 0° for 1 hour, then at RT for 2 hours. The reaction mixture is taken up in methylene chloride, washed, dried and evaporated to dryness to give, after purification by prep. TLC, N-methyl-N-[2-nitro-5-(2-chloro-4-trifluoromethylphenoxy)phenyl]ethoxycarbonyloxyamine.

nmr (CDCl$_3$) τ8.72 (t, 3H,OCH$_2$CH$_3$), 6.74 (S,3H,NCH$_3$), 5.82 (q,2H, OCH$_2$CH$_3$).

EXAMPLE 6

To a solution of N-methyl-N-[2-nitro-5-(2-chloro-4-trifluoromethylphenoxy)phenyl]hydroxyamine (600 mg, 1.65 mmol) in methylene chloride (4 ml) containing diisopropylethylamine (0.43 ml, 1.5 eq.) is added (2-methoxy)ethoxymethyl bromide (310 mg, 1.5 eq.) The mixture is stirred at RT for 16 hours. The reaction mixture is then taken up in methylene chloride, washed, dried, evaporated and purified by prep. TLC to yield N-methyl-N-[2-nitro-5-(2-chloro-4-trifluoromethylphenoxy)phenyl](2-methoxy)ethoxymethoxyamine (IXA, R is CH$_3$OCH$_2$CH$_2$OCH$_2$).

nmr (CDCl$_3$) τ6.87 (S,3H,NCH$_3$), 6.67 (S,3H,OCH$_3$), 6.59 (m,2H,—OCH$_2$CH$_2$OCH$_3$), 5.14 (S,2H,—OCH$_2$O—); m,2H,—OCH$_2$CH$_2$OCH$_3$).

EXAMPLE 7

Following the procedures of, for example, Example 3 or Example 5, each of the carboxylates under column I is reacted with N-methyl-N-[2-nitro-5-(2-chloro-4-trifluoromethylphenoxy)phenyl]hydroxyamine to yield the corresponding amine of formula IIA under column II.

I 1. methoxymethyl bromoacetate
2. methylthiomethyl bromoacetate
3. methylsulfinylmethyl bromoacetate
4. methylsulfonylmethyl bromoacetate
5. isopropyl bromoacetate
6. 2-propenyl bromoacetate
7. 2-propynyl bromoacetate
8. dimethylimino bromoacetate
9. 2-chloroethyl bromoacetate
10. methoxymethyl α-bromopropionate
11. methylthiomethyl α-bromopropionate
12. 2-propenyl α-bromopropionate
13. isopropyl α-bromopropionate
14. dimethylimino α-bromopionate
15. methyl methoxybromoacetate
16. ethyl methylthiobromoacetate

II $$\text{(IIA)}$$

Structure: 2-Cl, 4-(F$_3$C-phenoxy) substituted phenyl with NO$_2$ at position 2 and N(CH$_3$)—O—(CH)$_n$—C(=O)—O—R$^2$ group with R$^1$ substituent.

| | n | R$^1$ | R$^2$ |
|---|---|---|---|
| 1. | 1 | H | CH$_2$OCH$_3$ |
| 2. | 1 | H | CH$_2$SCH$_3$ |
| 3. | 1 | H | CH$_2$S(O)CH$_3$ |
| 4. | 1 | H | CH$_2$SO$_2$CH$_3$ |
| 5. | 1 | H | CH(CH$_3$)$_2$ |
| 6. | 1 | H | CH$_2$CH=CH$_2$ |
| 7. | 1 | H | CH$_2$C≡CH |
| 8. | 1 | H | N=C(CH$_3$)$_2$ |
| 9. | 1 | H | CH$_2$CH$_2$Cl |
| 10. | 1 | CH$_3$ | CH$_2$OCH$_3$ |
| 11. | 1 | CH$_3$ | CH$_2$SCH$_3$ |
| 12. | 1 | CH$_3$ | CH$_2$CH=CH$_2$ |
| 13. | 1 | CH$_3$ | CH(CH$_3$)$_2$ |
| 14. | 1 | CH$_3$ | N=C(CH$_3$)$_2$ |
| 15. | 1 | OCH$_3$ | CH$_3$ |
| 16. | 1 | SCH$_3$ | CH$_2$CH$_3$ |

EXAMPLE 8

Following the procedure of, for example, Example 4, each of the compounds under column III is reacted with N-methyl-N[2-nitro-5-(2-chloro-4-trifluoromethylphenoxy)phenyl]hydroxyamine to give the corresponding amine of formula IVA under column IV.

III 17. isobutyryl chloride
18. cyclopropylcarbonyl chloride
19. 4-chlorobenzoyl chloride
20. carbamoyl chloride
21. ethylthiocarbonyl chloride
22. 3-trifluoromethylanilinocarbonyl chloride
23. isocrotonyl chloride
24. 3-chloropropionyl chloride
25. chloroacetone
26. chloroacetophenone
27. 3-chloro-2-butanone

IV $$\text{(IVA)}$$

Structure analogous to IIA with N(CH$_3$)—O—(CH)$_n$—C(=O)—R$^4$ group and R$^3$ substituent.

| | n | R$^3$ | R$^4$ |
|---|---|---|---|
| 17. | 0 | — | CH(CH$_3$)$_2$ |
| 18. | 0 | — | C$_3$H$_5$ |
| 19. | 0 | — | C$_6$H$_4$(4-Cl) |
| 20. | 0 | — | N(CH$_3$)$_2$ |
| 21. | 0 | — | SCH$_2$CH$_3$ |
| 22. | 0 | — | NHC$_6$H$_4$(3-CF$_3$) |
| 23. | 0 | — | CH=CHCH$_3$ |
| 24. | 0 | — | CH$_2$CH$_2$Cl |
| 25. | 1 | H | CH$_3$ |
| 26. | 1 | H | C$_6$H$_5$ |
| 27. | 1 | CH$_3$ | CH$_3$ |

EXAMPLE 9

To a solution of N-methyl-N-[2-nitro-5-(2-chloro-4-trifluoromethylphenoxy)phenyl]hydroxyamine (700 mg, 1.93 mmol) in anhydrous THF (10 ml) is added methylisocyanate (220 mg, 2 eq.). The mixture is stirred at RT for 4 hours. The solvent and excess methlisocyanate are removed to yield N-methyl-N[2-nitro-5-(2-chloro-4-trifluoromethylphenoxy)phenyl](N-methyl)-carbamoyloxyamine.

EXAMPLE 10

To a solution of N-methyl-N-[2-nitro-5-(2-chloro-4-trifluoromethylphenoxy)phenyl]hydroxyamine (700 mg, 1.93 mmol) in methylene chloride (10 ml) containing triethylamine (0.32 ml, 1.29 eq.) is added N'-isopropylaminosulfonyl chloride (455 mg, 2.90 mmol). The mixture is stirred at RT overnight. The resulting reaction mixture is taken up in methylene chloride, washed, dried, evaporated to dryness and purified to yield N-methyl-N-[2-nitro-5-(2-chloro-4-trifluoromethylphenoxy)phenyl]-N'-isopropylaminosulfonyloxyamine.

In the same way, each of N'methylaminosulfonyl chloride and N'-N'-dimethylaminosulfonyl chloride is reacted with N-methyl-N-[2-nitro-5-(2-chloro-4-trifluoromethylphenoxy)phenyl]hydroxyamine to yield, respectively, N-methyl-N-[2-nitro-5-(2-chloro-4-trifluoromethylphenoxy)phenyl]-N'-methylaminosylfonyloxyamine, and N-methyl-N-[2-nitro-5-(2-chloro-4-trifluoromethylphenoxy)phenyl]-N',N'-dimethylaminosylfonyloxyamine.

EXAMPLE 11

To a solution of N-methyl-N-[2-nitro-5-(2-chloro-4-trifluoromethylphenoxy)phenyl]hydroxyamine (700 mg, 1.93 mmol) in THF (10 ml) containing triethylamine (1.2 eq.) is added chloromethylacetate (2 eq.). The mixture is stirred at RT overnight. Excess THF is removed and the product is evaporated to dryness and purified to give N-methyl-N-[2-nitro-5-(2-chloro-4-trifluoromethylphenoxy)phenyl]acetoxymethoxyamine.

In the same way, each of the carboxylates under column V is reacted with N-methyl-N-[2-nitro-5-(2-chloro-4-trifluoromethylphenoxy)phenyl]hydroxyamine to yield the corresponding amine of formula VIA under column VI.

| V |
|---|
| 28. chloromethyl t-butyrate |
| 29. chloromethyl cyclopropanecarboxylate |
| 30. chloromethyl cyclohexanecarboxylate |
| 31. α-chloroethyl acetate |
| 32. α-chloropropyl acetate |
| 33. α-chloroisobutyl acetate |
| 34. β-chloroethyl propionate |

VI

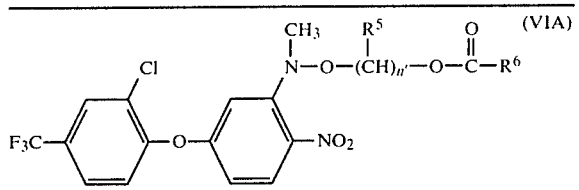

| | n' | $R^5$ | $R^6$ |
|---|---|---|---|
| 28. | 1 | H | $C(CH_3)_3$ |
| 29. | 1 | H | $C_3H_5$ |
| 30. | 1 | H | $C_6H_{11}$ |
| 31. | 1 | $CH_3$ | $CH_3$ |
| 32. | 1 | $CH_2CH_3$ | $CH_3$ |
| 33. | 1 | $CH(CH_3)_2$ | $CH_3$ |
| 34. | 2 | H | $CH_2CH_3$ |

EXAMPLE 12

Following the procedure of Example 3 or Example 6, each of the compounds under column VII is reacted with N-methyl-N-[2-nitro-5-(2-chloro-4-trifluoromethylphenoxy)phenyl]hydroxyamine to yield the corresponding amine of formula VIIIA under column VIII.

| VII |
|---|
| 35. methoxycarbonylmethyl bromoacetate |
| 36. methoxyethoxycarbonylmethyl bromoacetate |
| 37. 2-propenyloxycarbonylmethyl bromoacetate |
| 38. isopropoxycarbonylmethyl bromoacetate |
| 39. N,N—dimethylaminooxycarbonylmethyl bromoacetate |
| 40. dimethyliminooxycarbonylmethyl bromoacetate |
| 41. methylthiomethoxycarbonylmethyl bromoacetate |
| 42. ethoxycarbonylmethyl α-bromopropionate |
| 43. ethenyloxycarbonylmethyl bromopropionate |
| 44. methylthiomethoxycarbonylmethyl bromopropionate |
| 45. α-(methoxycarbonylethyl) bromoacetate |
| 46. α-(methoxycarbonylethyl)α-bromopropionate |
| 47. methoxycarbonylmethyl methoxybromoacetate |
| 48. ethoxycarbonylmethyl methylthiobromoacetate |
| 49. methoxycarbonylmethyl β-bromopropionate |

VIII

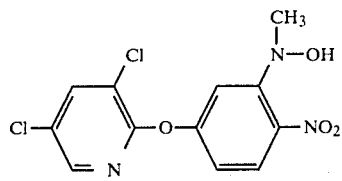

| | n' | $R^9$ | $R^{10}$ | $R^{11}$ | $R^{12}$ |
|---|---|---|---|---|---|
| 35. | 1 | H | H | H | $CH_3$ |
| 36. | 1 | H | H | H | $CH_2CH_2OCH_3$ |
| 37. | 1 | H | H | H | $CH_2CH=CH_2$ |
| 38. | 1 | H | H | H | $C(CH_3)_2$ |
| 39. | 1 | H | H | H | $NH(CH_3)_2$ |
| 40. | 1 | H | H | H | $N=C(CH_3)_2$ |
| 41. | 1 | H | H | H | $CH_2SCH_3$ |

VIII-continued

| | n' | $R^9$ | $R^{10}$ | $R^{11}$ | $R^{12}$ |
|---|---|---|---|---|---|
| 42. | 1 | $CH_3$ | H | H | $CH_2CH_3$ |
| 43. | 1 | $CH_3$ | H | H | $CH=CH_2$ |
| 44. | 1 | $CH_3$ | H | H | $CH_2SCH_3$ |
| 45. | 1 | H | $CH_3$ | H | $CH_3$ |
| 46. | 1 | $CH_3$ | $CH_3$ | H | $CH_3$ |
| 47. | 1 | $SCH_3$ | H | H | $CH_3$ |
| 48. | 1 | $SCH_3$ | H | H | $CH_2CH_3$ |
| 49. | 2 | H | H | H | $CH_3$ |

EXAMPLE 13

The compound, 4-(3,5-dichloropyridyl-2-oxy)-1,2-dinitrobenzene is used as the starting material in the procedure of Example 1 to yield N-methyl-N-[2-nitro-5-(3,5-dichloropyridyl-2-oxy)phenyl]-hydroxyamine.

EXAMPLE 14

A mixture of N-methyl-N[2-nitro-5-(2-chloro-4-trifluoromethylphenoxy)phenyl]hydroxyamine (700 mg., 1.93 mm) $K_2CO_3$ (320 mg.), 1-bromo-3,3-dimethylbutan-2-one (520 mg.) and acetone (10 ml.) is refluxed for about 16 hours. Then, the mixture is filtered and filtrate concentrated. The concentrate is purified by prep. TLC using 20% ethyl acetate/hexane to give N-methyl-N-[2-nitro-5-(2-chloro-4-trifluoromethylphenoxy)phenyl]t-butylcarbonylmethoxyamine (IVA; $R^3$ is H, n is one, and $R^4$ is t-butyl).

nmr ($CDCl_3$) τ 8.85(s,9H,t-butyl),6.87(S,3H,$NCH_3$), 5.47(S,2H,

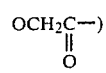

EXAMPLE 15

A mixture of N-methyl-N[2-nitro-5-(2-chloro-4-trifluoromethylphenoxy)phenyl]hydroxyamine (700 mg.), $K_2CO_3$ (320 mg.), allyl bromide (350 mg.) and acetone (10 ml) is refluxed for about 6 hours and then filtered. The filtrate is concentrated and purified by prep. TLC to give N-methyl-N-[2-nitro-5-(2-chloro-4-trifluoromethylphenoxy)phenyl]allyloxyamine (IXA; R is —CH₂—CH=CH₂)

nmr ($CDCl_3$) τ 6.95 (S,3H,$NCH_3$), 5.85 (d,2H,$OCH_2$—), 4.88 (m,2H,$CH_2$=), 4.14 (1H,=CH—$CH_2O$—).

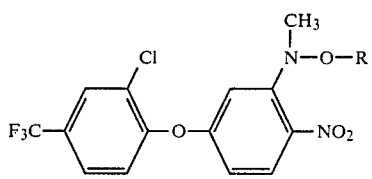

EXAMPLE 16

To a mixture of N-methyl-N[2-nitro-5-(2-chloro-4-trifluoromethylphenoxy)phenyl]hydroxyamine (700 mg.) in tetrahydrofuran (4 ml.) and benzene (2 ml) is added a drop of triethylamine and then methyl isocyanate (0.4 ml.). The mixture is then stirred at RT overnight. The mixture is then concentrated and purified by prep. TLC to give the carbamate (IVA; n is zero, $R^4$ is $CH_3NH-$).

nmr (CHCl$_3$) $\tau$ 7.17 (d,3H,NHC$\underline{H}_3$), 6.84 (S,3H,NCH$_3$), 3.44 (b,1H,N$\underline{H}$CH$_3$).

EXAMPLE 17

To a mixture of N-methyl-N[2-nitro-5-(2-chloro-4-trifluoromethylphenoxy)phenyl]hydroxyamine (600 mg.), CH$_2$Cl$_2$ (2 ml.), benzene (3 ml.) and pyride (0.16 ml.) is added cyclopropanecarboxylic acid chloride (0.23 ml.). The mixture is stirred at RT for about 4 hours and then concentrated. The concentrate is purified by prep TLC to give the cyclopropionyl hydroxyamine (IVA; n is zero and $R^4$ is cyclopropyl).

nmr (CDCl$_3$) $\tau$ 9.00 (m,4H,—CH$_2$CH$_2$—), 8.45 (m,1H,methine H), 6.75(S,3H,NCH$_3$)

EXAMPLE 18

Following the procedure of Example 15, each of ethyl bromide, benzyl bromide and chloroacetonitrile is reacted with N-methyl-N[2-nitro-5-(2-chloro-4-trifluoromethylphenoxy)phenyl]hydroxyamine to give N-methyl-N-[2-nitro-5-(2-chloro-4-trifluoromethylphenoxy)phenyl]ethoxyamine (IXA; R is ethyl), N-methyl-N-[2-nitro-5-(2-chloro-4-trifluoromethylphenoxy)phenyl]benzyloxyamine (IXA; R is benzyl), and N-methyl-N[2-nitro-5-(2-chloro-4-trifluoromethylphenoxy)phenyl]cyanomethoxyamine (IXA; R is CN—CH$_2$—), respectively.

EXAMPLE 19

Post-emergence herbicidal activity on the grasses (GR) green foxtail, watergrass, shattercane, and wild oats was tested for the compound of Example 1, 3 (first paragraph) and 5 by spraying seedlings with a solution of water/acetone 1:1), surfactant (1%) and test compound at a rate equivalent to 10 lb/acre. Each compound gave 100% of control.

EXAMPLE 20

Following the procedure of Example 14, benzoylmethyl bromide is reacted with N-methyl-N-[2-nitro-5-(2-chloro-4-trifluoromethylphenoxy)phenyl]hydroxyamine to give N-methyl-N-[2-nitro-5-(2-chloro-4-trifluoromethylphenoxy)phenyl]benzoylmethoxyamine (IVA; $R^3$ is H, n is one, and $R^4$ is phenyl).

EXAMPLE 21

A mixture of N-methyl-N-[2-nitro-5-(2-chloro-4-trifluoromethylphenoxy)phenyl]hydroxyamine (950 mg., 2.62 mm.), K$_2$CO$_3$ (434 mg), methyl bromoacetate (602 mg.) and acetone (20 ml.) is refluxed for about 16 hours. Then, the mixture is filtered and concentrated to give the methoxycarbonylmethoxyamine (IVA; $R^3$ is hydrogen, n is one, $R^4$ is methoxy). The foregoing ester is treated with 10% NaOH (10 ml.) in methanol (10 ml.) at RT for about 20 minutes. The mixture is then poured into water and extracted with ether. The aqueous phase is repeatedly extracted with ether and then combined extracts to give the free acid (IVA; $R^3$ is hydrogen, n is one, $R^4$ is hydroxy).

n m r (CDCl$_3$) $\tau$ 6.84(S,3H,NCH$_3$), 5.67(S,2H, 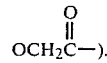 ).

The above-prepared acid is stirred with NaH (59 mg.,50% oil) and anhydrous ether (4 ml.) at RT for one hour. Solvent is removed, solid washed with pentane and dried in vacuum to yield the sodium salt.

EXAMPLE 22

To a solution of N-methyl-N-[2-nitro-5-(2-chloro-4-trifluoromethylphenoxy)phenyl]hydroxyamine methoxycarbonylmethylamine (868 mg.) and hydrous stannous chloride (2.25 g.) in methanol (40 ml.) is added, at 60°, sodium borohydride (30 mg) in methanol over a period of about 20 minutes. After addition, the reaction mixture is stirred for about 30 minutes, then cooled to 5°–10° and water is added, followed by neutralization with dilute NaOH. The methanol is evaporated off and the aqueous solution is extracted with methylene chloride. The extracts are combined, washed, dried and evaporated to dryness to give N-methyl-N-[2-amino-5-(2-chloro-4-trifluoromethylphenoxy)phenyl]methoxycarbonyl methoxyamine (XA).

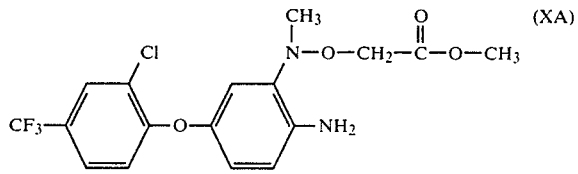

The above 2-amino compound (XA) is diazotized following the procedure described in Org. Syth. Coll. Vol. 1: 514 (1932). The resulting diazo salt is treated with cuprous cyanide (1.2 eq.) in benzene-water solution to give N-methyl-N-[2-cyano-5-(2-chloro-4-trifluoromethylphenoxy)phenyl]methoxycarbonylmethoxyamine. By reacting the diazo salt with cuprous chloride (1.2 eq.), there is prepared N-methyl-N-[2-chloro-5-(2-chloro-4-trifluoromethylphenoxy)phenyl]methoxycarbonylmethoxyamine.

EXAMPLE 23

A mixture of N-methyl-N-[2-nitro-5-(2-chloro-4-trifluoromethylphenoxy)phenyl]hydroxyamine (500 mg, 1.38 mmol), K$_2$CO$_3$ (228 mg), methyl iodide (0.5 ml) and acetone (15 ml) is heated under reflux for 8 hours. It is then filtered and concentrated, and the residue is taken up in methylene chloride, dried and concentrated to dryness. The crude product is purified by prep. TLC to give N-methyl-N-[2-nitro-5-(2-chloro-4-trifluoromethylphenoxy)phenyl]methoxyamine (IXA; R is methyl). MS 376 (M+).

nmr (CDCl₃) τ 6.97 (s, 3H, NCH₃), 6.47 (s, 3H, OCH₃).

EXAMPLE 24

A. A mixture of 4-(3-chloro-5-trifluoromethyl-2-pyridyloxy)-1,2-dinitrobenzene (2.50 g, 6.88 mmol), N-methylhydroxyamine (1.15 g), K₂CO₃ (1.14 g, 8.26 mmol) and THF (20 ml) is stirred at RT for 48 hours. The reaction mixture is filtered and the filtrate is concentrated. The resulting residue is taken up in CH₂Cl₂, washed, dried and evaporated to give N-methyl-N-[2-nitro-5-(3-chloro-5-trifluoromethyl-2-pyridyloxy)-phenyl]-hydroxyamine (IXB; R is H).

nmr (CDCl₃) τ 6.89 (s, 3H, N—CH₃); 3.14 (dd, 9 Hz, 1H), 2.77 (d, 2 Hz, 1H), 2.10 (d, 2 Hz, 1H,)-aromatic H; 2.07 (d, 2 Hz, 1H), 1.77 (d, 2 Hz, 1H,)-pyridine H.

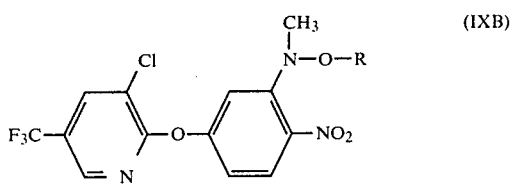

(IXB)

B. To the above hydroxyamine (600 mg, 1.65 mmol) is added K₂CO₃ (273 mg, 1.98 mmol), methyl iodide (0.5 ml) and acetone (15 ml), and the mixture is heated under reflux for 5 hours. The reaction mixture is filtered, the filtrate is concentrated, and the residue is taken up in CH₂Cl₂, washed, dried and evaporated to dryness. The crude product is purified by prep. TLC to yield N-methyl-N-[2-nitro-5-(3-chloro-5-trifluoromethyl-2-pyridyloxy)phenyl]methoxyamine (IXB; R is —CH₃).

nmr (CDCl₃) τ 6.90 (s, 3H, N—CH₃), 6.40 (s, 3H, OCH₃); 3.07 (dd, 9 Hz, 1H), 2.67 (d, 2 Hz, 1H), 2.17 (d, 9 Hz, 1H,)-aromatic H,; 2.04 (d, 2 Hz, 1H), 1.74 (d, 2 Hz, 1H,)-pyridine H.

EXAMPLE 25

Following the procedure of Example 24B, N-methyl-N-[2-nitro-5-(3-chloro-5-trifluoromethyl-2-pyridyloxy)-phenyl]hydroxyamine is reacted with each of allyl bromide, benzyl bromide, methyl bromoacetate and 1-bromo-3,3-dimethylbutan-1-one to yield, respectively, N-methyl-N-[2-nitro-5-(3-chloro-5-trifluoromethyl-2-pyridyloxy)phenyl]allyloxyamine (IXB; R is —CH₂—CH=CH₂);

N-methyl-N-[2-nitro-5-(3-chloro-5-trifluoromethyl-2-pyridyloxy)phenyl]benzyloxyamine (IXB; R is benzyl);

N-methyl-N-[2-nitro-5-(3-chloro-5-trifluoromethyl-2-pyridyloxy)phenyl]methoxycarbonylmethoxyamine (IXB; R is —CH₂—C(O)—OCH₃); and N-methyl-N-[2-nitro-5-(3-chloro-5-trifluoromethyl-2-pyridyloxy)-t-butylcarbonylmethoxyamine (IXB; R is —CH₂—C(O)—C(CH₃)₃).

EXAMPLE 26

Following the procedure of Example 16, N-methyl-N-[2-nitro-5-(3-chloro-5-trifluoromethyl-2-pyridyloxy)-phenyl]hydroxyamine and methyl isocyanate are reacted together to give the corresponding carbamate (IXB; R is —C(O)—NH—CH₃).

EXAMPLE 27

Following the procedure of Example 17, N-methyl-N-[2-nitro-5-(3-chloro-5-trifluoromethyl-2-pyridyloxy)-phenyl]hydroxyamine is reacted with cyclopropanecarboxylic acid chloride to give N-methyl-N-[2-nitro-5-(3-chloro-5-trifluoromethyl-2-pyridyloxy)phenyl]-cyclopropionylhydroxyamine (IXB; R is —C(O)—C₃H₅).

EXAMPLE 28

A mixture of 4-(3,5-dichloro-2-pyridyloxy)-1,2-dinitrobenzene (800 mg, 2.42 mmol), N-methylhydroxyamine (472 mg, 4.84 mmol), K₂CO₃ (400 mg, 2.90 mmol) and THF (10 ml) is stirred at RT for 48 hours. The reaction mixture is filtered, and the filtrate is concentrated and then taken up in methylene chloride, washed, dried and evaporated to give N-methyl-N-[2-nitro-5-(3,5-dichloro-2-pyridyloxy)phenyl]-hydroxyamine, a crystalline solid.

The above hydroxyamine (~800 mg) is dissolved in methylene chloride (15 ml). Pyridine (0.3 ml, 1.5 eq.) and methyl chloroformate (0.3 ml, 1.6 eq.) are then added, and the resulting mixture is stirred at RT for 2 hours. The reaction mixture is diluted with methylene chloride, washed, dried and evaporated to dryness. The crude product is purified by prep. TLC to give N-methyl-N-[2-nitro-5-(3,5-dichloro-2-pyridyloxy)phenyl]methoxycarbonyloxyamine.

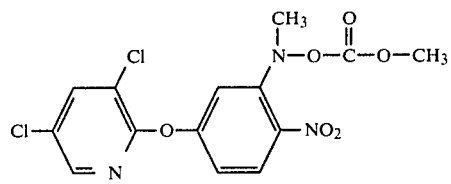

nmr (CDCl₃) τ 6.72 (s, 3H, N—CH₃), 6.19 (s, 3H, O—CH₃); 2.94 (dd, 8 Hz, 1H), 2.65 (d, 2 Hz, 1H), 2.09 (d, 8 Hz, 1H,)-aromatic H; 2.20 (d, 2 Hz, 1H) and 2.00 (d, 2 Hz, 1H,)-pyridine H.

EXAMPLE 29

A mixture of 4-(2-chloro-4-trifluoromethylphenoxy)-1,2-dinitrobenzene (1000 mg, 2.76 mmol), methoxyamine hydrochloride (362 mg, 5.52 mmol), potassium carbonate (762 mg, 5.52 mmol), and THF (15 ml) is stirred at RT for 4 days. The reaction mixture is then filtered, and the filtrate is concentrated to dryness. The crude residue is taken up in ether, washed, dried and evaporated to dryness to give, after purification by column chromatography, N-(2-nitro-5-(2-chloro-4-trifluoromethylphenoxy)phenyl]methoxyamine (XIV; R'=H), m.p. −105°.

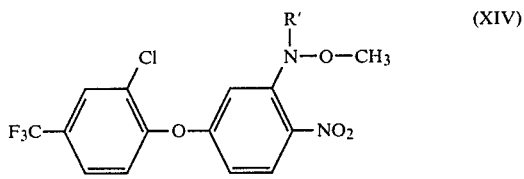

(XIV)

EXAMPLE 30

Following the procedure of Example 29, each of 4-(4-trifluoromethylphenoxy)-1,2-dinitrobenzene, 4-(2-fluoro-4-trifluoromethylphenoxy)-1,2-dinitrobenzene, 4-(4-chloro-2-nitrophenoxy)-1,2-dinitrobenzene and 4-(2,6-dichloro-4-trifluoromethylphenoxy)-1,2-dinitrobenzene is reacted with methoxyamine hydrochloride to yield, respectively, N-[2-nitro-5-(4-trifluoromethylphenoxy)phenyl]methoxyamine, N-[2-nitro-5-(2-fluoro-4-trifluoromethylphenoxy)phenyl]methoxyamine, N-[2-nitro-5-(4-chloro-2-nitrophenoxy)phenyl]methoxyamine, and N-[2-nitro-5-(2,6-dichloro-4-trifluoromethylphenoxy)phenyl]methoxyamine.

EXAMPLE 31

To a solution of N-[2-nitro-5-trifluoromethylphenoxy)phenyl]methoxyamine (660 mg, 1.82 mmol) in methylene chloride (10 ml) is added, at 0°, triethylamine (0.5 ml, 3.64 mmol) and methylchloroformate (0.3 ml). The resulting mixture is stirred at RT for 16 hours. The reaction mixture is poured into water and extracted with ether. The extracts are combined and washed, dried and evaporated to dryness. The crude product is purified by prep. TLC to give N-[2-nitro-5-trifluoromethylphenoxy)phenyl]-N-methoxycarbamate (XIV;

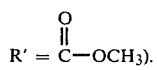

nmr (CDCl$_3$) τ 6.24 (s, 3H, O—CH$_3$) and 6.19 (s, 3H, C(O)OCH$_3$).

IR (film) = 1730 cm$^{-1}$ (C(O)OCH$_3$).

EXAMPLE 32

A. A mixture of the methoxyamine of Example 29 (530 mg, 1.46 mmol), methyl bromoacetate (0.27 ml, 2.92 mmol), potassium carbonate (303 mg, 2.19 mmol) and acetone (10 ml) is heated under reflux for 4 hours. The reaction mixture is filtered, and the filtrate is concentrated to yield, after purification by prep. TLC, N-methoxycarbonylmethyl-N-[2-nitro-5-(2-chloro-4-trifluoromethylphenoxy)phenyl]methoxyamine (XIV;

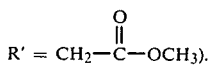

B. Following the same procedures, the methoxyamine of Ex. 29 is reacted with methyl 3-bromopropionate to give N-methoxycarbonylethyl-N-[2-nitro-5-(2-chloro-4-trifluoromethylphenoxy)phenyl]methoxyamine (XIV;

C. Following the procedure of Example 29, N-[2-nitro-5-(2-chloro-4-trifluoromethylphenoxy)phenyl]ethoxyamine is prepared from 4-(2-chloro-4-trifluoromethylphenoxy)1,2-dinitrobenzene and ethoxyamine hydrochloride. The resulting N-phenylethoxyamine is then reacted with methyl bromoacetate, following the methods of this example, to yield N-methoxycarbonylmethyl-N-[2-nitro-5-(2-chloro-4-trifluoromethylphenoxy)phenyl]ethoxyamine.

EXAMPLE 33

A mixture of the methoxyamine of Example 29 (600 mg, 1.65 mmol), t-butyl bromoacetate (0.4 ml, 2.48 mmol), potassium carbonate (274 mg, 1.98 mmol) and 2-butanone (15 ml) is heated under reflux for 3 hours. It is then filtered, and the filtrate is concentrated and taken up in ether, washed, dried and evaporated to dryness. The crude product is purified by prep. TLC to give N-t-butoxycarbonylmethyl-N-[2-nitro-5-(2-chloro-4-trifluoromethylphenoxy)phenyl]-methoxyamine (XIV;

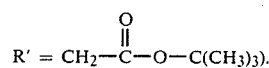

nmr (CDCl$_3$) τ8.54 (s, 9H, C(CH$_3$)$_3$), 6.40 (s, 3H, N—OCH$_3$), 6.10 (s, 2H, N—CH$_2$—).

IR (film) = 1740 cm$^{-1}$ (C(O)O—).

EXAMPLE 34

To a solution of the methoxyamine of Example 29 (500 mg, 1.38 mmol) in methylene chloride (10 ml) in the presence of triethylamine (0.38 ml, 2.76 mmol) is added dropwise at 0° ethoxymalonylchloride (311 mg, 0.26 ml, 2.07 mmol) in methylene chloride (5 ml). After addition is complete, the mixture is stirred at RT overnight. The reaction mixture is poured into water and extracted with methylene chloride. The combined extracts are washed, dried and evaporated to dryness to give, after purification by prep. TLC, N-(ethoxymalonyl)-N-[2-chloro-4-trifluoromethylphenoxy)phenyl]methoxyamine (XIV;

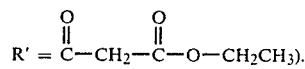

nmr (CDCl$_3$) τ 8.74 (t, 3H, OCH$_2$CH$_3$), 6.37 (s, 2H, C(O)CH$_2$C(O)), 6.24 (s, 3H, N—OCH$_3$), 5.84 (q, 2H, OCH$_2$ CH$_3$).

IR (film) = 1695, 1740 cm$^{-1}$ (C(O)CH$_2$C(O)O).

EXAMPLE 35

Acetone (0.6 ml) is added to a solution of the methoxyamine of Example 29 (500 mg, 1.38 mmol) in pyridine (5 ml). The resulting mixture is stirred at RT overnight, after which it is diluted with methylene chloride and acidified. The phases are separated, and the organic phase is washed, dried and evaporated. The crude product is purified by prep. TLC to yield N-[2-nitro-5-(2-chloro-4-trifluoromethylphenoxy)phenyl]-N-methoxyacetamide (XIV;

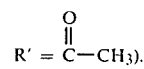

nmr (CDCl$_3$) τ 7.74 (s, 3H, C(O)CH$_3$), 6.24 (s, 3H, N—OCH$_3$).

IR (film) = 1690 cm$^{-1}$ (C(O)CH$_3$).

EXAMPLE 36

Following the procedure of Example 29, 4-(3-chloro-5-trifluoromethyl-2-pyridyloxy)-1,2-dinitrobenzene and methoxyamine hydrochloride are reacted together to give N-[2-nitro-5-(3-chloro-5-trifluoromethyl-2-pyridyloxy)phenyl]methoxyamine (XV; R′=H).

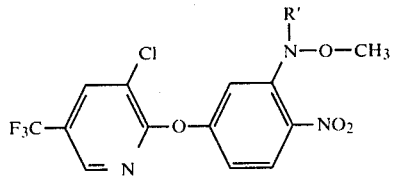 (XV)

Following the procedure of, for example, Example 30 or 31, the above phenylmethoxyamine is reacted with each of methyl bromoacetate, methyl chloroformate, allyl bromide and t-butyl bromoacetate to yield, respectively, N-methoxycarbonylmethyl-N-[2-nitro-5-(3-chloro-5-trifluoromethyl-2-pyridyloxy)phenyl]methoxyamine (XV; R′=

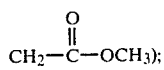);

N-[2-nitro-5-(3-chloro-5-trifluoromethyl-2-pyridyloxy)-phenyl]methoxycarbamate (XV;

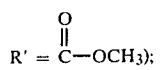);

N-prop-2-enyl-N-[2-nitro-5-(3-chloro-5-trifluoromethyl-2-pyridyloxy)phenyl]methoxyamine (XV; R′=CH₂—CH=CH₂); and N-t-butoxycarbonylmethyl-N-[2-nitro-5-(3-chloro-5-trifluoromethyl-2-pyridyloxy)phenyl]methoxyamine (XV; R′=

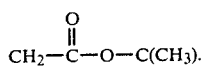.

EXAMPLE 37

Post-emergence herbicidal activity on the grasses (GR) green foxtail, watergrass, shattercane and wild oats and on the broadleafs (BL) annual morning glory, mustard, soybean and velvetleaf was tested for the compound of each of Examples 23, 24B, 31 and 32A (test compounds no. 4, 5, 6 and 7) by spraying seedlings with a solution of water/acetone (1:1), surfactant (1%) and test compound at a rate of equivalent to 10 lb/acre. The average score is given, in percent control, in Table A below.

Pre-emergence herbicidal activity of test compounds 4, 5, 6 and 7 was tested on the above grasses and broadleafs (except that nightshade was substituted for soybean) at a rate equivalent to 10 lb/acre. The average activity, in percent control, is given in Table A.

TABLE A

| Test Compound | Post | | Pre | |
|---|---|---|---|---|
| | GR | BL | GR | BL |
| 4 | 100 | 100 | 100 | 92 |
| 5 | 100 | 92 | 100 | 93 |
| 6 | 98 | 98 | 91 | 89 |
| 7 | 100 | 98 | 89 | 100 |

EXAMPLE 38

Following the procedure of Example 30 or 35, each of methoxyethyl bromoacetate, isopropyl bromoacetate and i-butyl bromoacetate is reacted with N-[2-nitro-5-(2-chloro-4-trifluoromethylphenoxy)phenyl]methoxyamine to yield:

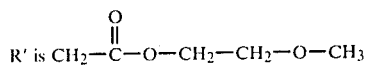 (XIV)

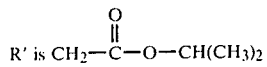 (XIV)

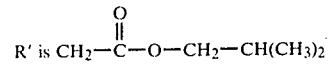 (XIV)

The above structures were confirmed by NMR.

What is claimed is:

1. A compound of the following formula (A):

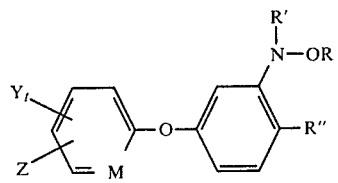

wherein
M is N;
t is zero, one or two;
each of Y and Z is independently selected from hydrogen, lower alkyl, lower haloalkyl, or halogen;
R′ is lower alkyl;
R″ is nitro, amino, cyano or chloro;
R is the group

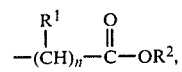, wherein,
n is zero, one or two;
R¹ is hydrogen, methyl, methoxy or methylthio;
R² is hydrogen, sodium cation, lower alkyl, lower alkenyl, lower alkynyl, lower alkylthioalkyl, lower alkoxyalkyl, lower alkylsulfinylalkyl, lower alkylsulfonylalkyl, unsubstituted phenyl, cycloalkyl having 3 to 8 carbon atoms, lower haloalkyl, lower alkoxyalkoxyalkyl, lower alkylamino, lower dialkylamino, or N=C(R⁸)₂; and
R⁸ is lower alkyl.

2. A compound according to claim 1 of the formula:

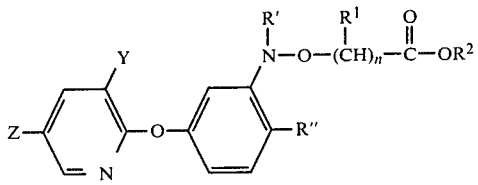

in which n is zero or one, R¹ is hydrogen or methyl and R² is lower alkyl or lower alkoxyalkyl.

3. A compound according to claim 2 wherein n is one, R¹ is hydrogen or methyl, R′ is methyl, R″ is nitro, Y is hydrogen or chloro and Z is chloro or trifluoromethyl.

4. A compound according to claim 3 wherein $R^1$ is hydrogen, $R^2$ is lower alkyl and Z is trifluoromethyl.

5. The compound according to claim 4 wherein n is one, R' is methyl, R" is nitro, $R^1$ is hydrogen, $R^2$ is methyl, Y is chloro and Z is trifluoromethyl.

6. A compound according to claim 3 wherein $R^1$ is hydrogen, $R^2$ is lower alkoxyalkyl and Z is trifluoromethyl.

7. A herbicidal composition which comprises a herbicidally effective amount of a compound according to claim 1 and a suitable carrier material.

8. A method for the control of weeds which comprises applying to the locus of the weeds a herbicidally effective amount of a compound according to claim 1.

* * * * *